United States Patent [19]

Walker

[11]  4,386,962

[45]  Jun. 7, 1983

[54] COMPOSITION AND METHOD FOR PRODUCING CERAMIC ARTICLES

[76] Inventor: William F. Walker, 422 Robney St., Sumter, S.C. 29150

[21] Appl. No.: 186,497

[22] Filed: Sep. 12, 1980

[51] Int. Cl.³ .......................... C09K 3/00; C04B 33/13
[52] U.S. Cl. ...................................... 106/35; 433/222; 433/228; 501/147
[58] Field of Search .......................... 106/39.5, 45, 35; 433/222, 228; 501/147

[56] References Cited

U.S. PATENT DOCUMENTS

| | | | |
|---|---|---|---|
| 1,398,014 | 11/1921 | Falton | 501/147 |
| 1,745,102 | 1/1930 | Lambic et al. | 501/147 |
| 1,899,584 | 2/1933 | Navies | 106/73.5 |
| 2,268,131 | 12/1941 | Barker et al. | 501/147 |
| 2,686,131 | 8/1954 | Combs | 106/48 |
| 2,890,964 | 6/1959 | Commons, Jr. et al. | 106/48 |
| 3,037,828 | 6/1962 | Michael | 106/48 |

OTHER PUBLICATIONS

Kingery et al., *Ceramic Fabrication Processes*, Part I Slip Casting, pp. 15–19, 28–30 & 42, published by "The Technology Press of MIT & John Wiley & Sons N.Y., 1958, Library of Congress Card No. 58–6077.
Dodd, A; "Dictionary of Ceramics", published by Philosophical Library N.Y. 1964 pp. 80 & 116.

*Primary Examiner*—Mark Bell
*Attorney, Agent, or Firm*—Dennison, Meserole, Pollack & Scheiner

[57] ABSTRACT

A composition is disclosed for use in forming ceramic articles having improved color, density, bonding strength and mechanical strength. Ceramic particles are slurried with a composition that tends to minimize inclusion of bubbles of gas, e.g., air, and also minimize interstitial voids between the ceramic particles. In a preferred mode, the ceramic particles are slurred with an aqueous solution of sodium hydroxide having, for example, a sodium hydroxide concentration, by weight, in the order of about 0.02% to about 0.03%. The aqueous solution of the sodium hydroxide is added to a powered ceramic until a workable past or slurry is obtained. Articles are formed using the paste or slurry or the paste or slurry is built-up on a support and the ceramic is then fired to fuse the particles.

2 Claims, No Drawings

COMPOSITION AND METHOD FOR PRODUCING CERAMIC ARTICLES

BACKGROUND OF THE INVENTION

The invention generally relates to a liquid medium for producing a paste or slurry of powdered ceramic material from which fired ceramic articles or ceramic coated articles, having improved properties are produced.

More particularly, the invention relates to a method and a liquid medium for producing fired ceramics having improved density, color intensity, mechanical strength, and substrate to ceramic bond strength.

The method of the present invention is particularly suitable for the preparation of procelain pastes or slurries of the type employed by dental technicians in making dental appliances such as porcelain jacketed crowns, and the like.

It has been the standard practice for many years to utilize distilled water as a building medium, i.e., a transient binding agent, to enable laying-up or building-up of porcelain mix such as to a metal foundation of a dental appliance. While the use of water in forming a slurry of procelain powder has come to be a rather standard practice in the art, it is recognized that such practice is not without problems.

A significant problem is that shrinkage and distortion of a water slurry of porcelain powder, such as applied to a metal dental appliance foundation, often occurs upon firing. Additives have been tried in the wetting stage to develop green-biscuit, i.e. pre-fired, strength, and to minimize distortion and U.S. Pat. No. 3,973,970 is typical of such prior art attempts. However, the additive disclosed in U.S. Pat. No. 3,973,970 includes a component that is not transient which comprises a colloidal silica flux thereby providing a non-homogeneous fired porcelain.

Another problem is that as the porcelain slurry is applied to a metal foundation of a dental appliance, it tends to dry out whereby shrinkage or distortion occurs even before firing. U.S. Pat. No. 3,880,662 is typical of prior art directed to providing aqueous transient bonding agents that are intended to delay drying out by slowing down loss of water. While such attribute of the binding agent of U.S. Pat. No. 3,880,662 is not unlike one attribute of the practice of the present invention, i.e., keeping the porcelain mix wetter longer, such does not materially enhance the workability of the composition disclosed in the patent since the composition does not substantially eliminate the need to vibrate the porcelain mix as is generally the instance in the practice of the present invention.

Still another of the problems is that as the porcelain mix is applied to the metal foundation of a dental appliance, it is necessary to vibrate the mix on the surface being covered to insure that the porcelain particles move as closely together as possible to attempt to minimize shrinkage of the ceramic upon firing.

SUMMARY OF THE INVENTION

It has now been found that the problems attendant the use of known transient binding agents for the particulate precursors for fired ceramics can substantially be overcome by utilizing a transient liquid binding agent that establishes an ionically charged environment that causes ceramic precursor particles slurried therein to move more closely together so that a more dense, stronger and more highly colored ceramic material is obtained from the particulate ceramic precursor.

It will be understood that the term ceramic as used herein defines any product made essentially from a, generally particulate, non-metallic mineral by firing at high temperature. By way of non-limiting example, the term ceramic as used herein would include products commonly known as porcelain, stoneware, whiteware, tile, glazes, slips, electric insulators, etc. For purposes of the present disclosure, the term ceramic is to be understood to also include particulate glass as may be utilized to prepare a frit, or the like, such as comprising a glaze to be utilized to produce a vitreous coating on finished pottery or enamelware, for example.

While it is not to be taken in a limiting sense, it is theorized that the use of an appropriate electrolyte as a transient binding agent causes the slurried porcelain powder articles to have imposed upon them, by a mechanism not presently fully understood, random, but apparently rather evenly distributed positive and negative electrical surface charges. The oppositely charged porcelain particles tend to move more closely together than they otherwise would. The charge-induced attraction of the porcelain particles together with an increased surface tension effect provided by the electrolyte apparently tends to assist in generally eliminating microscopic gas bubbles and maintaining the closely aggregated porcelain particles in relatively intimate contact as a disperse phase with relatively small interstitial voids therebetween. The interstitial voids that remain are taken up by the electrolyte which forms the continuous phase until volitized off into the ambient or the ambient of a furnace, such as a muffle furnace, during firing.

It is thus theorized that the relatively dense packing of the ceramic precursor particles by the practice of the present invention enables the production of fired ceramic of increased density, and thus mechanical strength, uniformity of color, and bonding strength.

With the foregoing in mind, it is accordingly an object of the present invention to provide a binding agent for ceramic precursors, e.g., porcelain and the like, which avoids the drawbacks of the prior art.

It is further an object of the present invention to provide a building medium and method that assists in bringing particulate ceramic precursor, porcelain, powder, particles together during build-up of a ceramic article such as a porcelain dental appliance.

It is still a further object of the present invention to provide a composition, and method of using the same, that insures that porcelain particles brought together during build-up of a porcelain dental appliance tend to remain aggregated.

It is another object of the present invention to provide a building medium that substantially eliminates a need for vibrating a porcelain powder mix such as during build-up of a dental appliance.

It is still another object of the present invention to provide a building medium, or transient additive composition, for making porcelain dental appliances wherein the density and color of the fired porcelain is improved and shrinkage upon firing is minimized.

These and other objects are achieved with a building medium, or generally transient additive composition, that tends to move close together the ceramic precursor particles slurried in the building medium. The present invention in providing an improved green strength and improved fired ceramic articles relies on closely associating, or agglomerating the ceramic precursor particles before firing substantially without a need for vibrating as the articles are being formed.

In a broad sense, the present invention resides in establishing suitable ionic charges at the surfaces of the ceramic precursor particles whereby the particles are closely and densely agglomerated during build-up substantially without a need for vibrating.

The building medium or transient additive composition is added directly to the powdered ceramic precursor as a substitute for distilled water and is believed to function by establishing attractive ionic forces that tend to enhance aggregation of the porcelain particles without detrimentally shortening working time.

In a preferred exemplary mode, the present invention contemplates the use of an electrolytic solution to enhance aggregation of porcelain particles used for forming porcelain dental appliances. In this regard, a preferred electrolytic solution comprises an approximately 0.02% to approximately 0.03% solution of sodium hydroxide. The electrolyte may be dissolved or suspended in any suitable liquid medium, but deionized or distilled water is preferred. It will be appreciated that the specific electrolytic solution concentration may selectively be varied as long as the aforedescribed condition exists whereby the porcelain particles are attracted closely to each other, and maintained in such relationship through firing.

DETAILED DESCRIPTION OF PREFERRED EMBODIMENTS

In the following examples, certain formulations are given to illustrate preferred embodiments of the invention. It is understood, however, that variations from these specific formulations can be made without departing from the scope of the appended claims.

EXAMPLE 1

An approximately 0.03% aqueous solution of sodium hydroxide was prepared by dissolving commercial grade sodium hydroxide, i.e., 76% $Na_2O$, in distilled water. An exemplary working amount of sodium hydroxide solution may thus be prepared by dissolving approximately 7.5 grams of sodium hydroxide in approximately 250 Ml distilled water.

A dental crown cast from a suitable dental gold alloy was first provided with an opacifying ceramic coating consisting of titanium dioxide slurried in the 0.03% aqueous solution of sodium hydroxide which was added on a drop-wise basis until the titanium dioxide was of a consistency suitable for being applied by spatula or brush.

After coating of the required surfaces of the crown with the titanium dioxide slurry, the crown was fired in a vacuum muffle furnace at a temperature in the order of 1760° F. to about 1800° F. thereby providing an opaque ceramic coating upon the crown. The opaque titanium dioxide-base ceramic was found to be characterized by improved density and adhesion and more significantly outgassing from the cast crown apparently was absorbed, or adsorbed, in the densified titanium dioxide opacifying ceramic coating since the coating was of uniform color.

The body layer of the porcelain on the crown was prepared by slurrying of approximately 3 grams of commercially available porcelain powder with about 4 to 5 drops of the 0.03% sodium hydroxide building medium which was added a drop at a time.

The slurried porcelain particles were then brushed onto, i.e., built-up on, the opacified crown and it was found that the porcelain precursor particles had autogenously densified to the extent that it was not necessary to vibrate the crown during the build-up, or for that matter, to "blot" the built-up ceramic precursor to remove excess building medium.

The crown was then refired in a conventional vacuum muffle furnace, such as operated at 28 to 30 inches of mercury, at a slightly lower temperature than previously, i.e., 1740° F. to 1780° F. to fuse the body forming porcelain precursor particles to one another and to the underlying opacifying titanium dioxide ceramic.

The fired body layer ceramic was analyzed with a photometer, as conventionally used for determining the color hue of ceramics, and it was found that the hue was some 40 points lower on the photometer scale than without the use of the building medium of the present invention. It will be understood that a reading of 40 points "lower" is indicative of a deeper hue as is deemed to be indicative of the closer packing, i.e., higher density, of the particles comprising the ceramic.

EXAMPLE 2

The procedure of Example 1 was repeated with the exception that a 0.01% solution of sodium hydroxide was used in lieu of the sodium hydroxide solution used in Example 1.

It was found that the desired effect of densifying the ceramic precursor particles was not achieved and that there was in fact a tendency for the slurry to "run" despite the use of comparable amounts of the sodium hydroxide solution in slurrying both the titanium dioxide opacifying ceramic layer precursor particles and the porcelain precursor powder used to form a porcelain body layer.

Further, the increased degree or color hue discernible by photometric analysis as in Example 1 was not present with respect to a porcelain jacketed crown as produced in accordance with this Example.

EXAMPLE 3

The procedure of Example 1 was reproduced with the exception that an approximately 0.2% aqueous solution of sodium hydroxide was used.

It was found that the titanium dioxide slurry and porcelain slurries were such as were suitable for working, i.e., they could be spread or brushed without need for vibrating or blotting, and upon firing, produced improved opacifying and body ceramics, but were characterized by not affording adequate working time to enable build-up of the ceramic precursor without taxing the ceramist.

Further, analysis of the finished crown by photometric means determined that the ceramic was of higher than usual density as deduced by a higher than customary color hue.

EXAMPLE 4

The procedure of Example 1 was reproduced with the exception that approximately 0.04% aqueous solution of sodium hydroxide was used in lieu of the sodium hydroxide solution of Example 1.

It was found that the slurry produced requires too long a period of "volitization" heating in the vacuum muffle furnace thereby causing "boiling" of the nonvaporized building medium within the porcelain thereby causing "chalking", i.e., microscopic porosity in the ceramic layers produced.

It will be appreciated that such condition is highly undesirable.

EXAMPLE 5

For additional comparative test purposes, two buttons of dental non-precious metal were cast. One button was "jacketed" in accordance with the procedure of Example 1 and the other button was jacketed in accordance with the procedure of Example 1 with the exception that distilled water was used in lieu of the aqueous solution of sodium hydroxide.

It was found that the button produced in accordance with the procedure of Example 1 was not characterized by "greening", i.e., contaminant gases, penetrating through the titanium dioxide ceramic opacifying layer and consequently, the porcelain body layer was likewise free of any greening.

Quite to the contrary, on the "control" button, in conjunction with which no aqueous sodium hydroxide solution was utilized, greening was quite evident to the extent that the ceramic jacket produced is unsatisfactory. Furthermore, photometric analysis of the two test buttons shows that the color hue of the test button produced in accordance with the procedure of Example 1 is some 40 points lower than the color hue of the ceramic of the other test button.

From the foregoing, it will be seen that the practice of the present invention provides improved ceramics characterized by increased density, mechanical strength, color hue, and strength of bond to a metallic substrate or adjacent ceramic layer.

It will be appreciated that the foregoing is exemplary and that various modifications may be made without departing from the invention as defined in the appended claims.

I claim:

1. A ceramic composition consisting essentially of a particulate dental porcelain precursor and an amount of a transient binder sufficient for providing a paste for building up a green porcelain precursor layer on a dental appliance to be jacketed with dental porcelain said transient binder consisting essentially of an aqueous solution of about 0.02% to about 0.03% by weight of sodium hydroxide.

2. In the method of making fired dental porcelain articles comprising the steps of preparing an aqueous suspension of a particulate dental porcelain precursor, forming the suspension, and firing the formed suspension to fuse the precursor to form a dental porcelain article the improvement comprising said aqueous suspension being prepared by forming a paste of said particulate dental porcelain precursor and an aqueous solution of about 0.02% to about 0.03% by weight of sodium hydroxide wherein upon firing a dental porcelain article of improved density, color hue and minimized shrinkage is produced.

* * * * *